United States Patent [19]

Spector et al.

[11] Patent Number: 5,128,365
[45] Date of Patent: Jul. 7, 1992

[54] COMPOUNDS HAVING GLUTATHIONE PEROXIDASE ACTIVITY AND USE THEREOF

[75] Inventors: Abraham Spector, New York, N.Y.; Stephen R. Wilson, Chatham; Paul A. Zucker, Maplewood, both of N.J.

[73] Assignees: The Trustees of Columbia University in the City of New York; New York University, both of New York, N.Y.

[21] Appl. No.: 383,189

[22] Filed: Jul. 19, 1989

[51] Int. Cl.[5] .................. C07C 403/12; C07D 319/02; A61K 31/40; A61K 31/095
[52] U.S. Cl. .................................. 514/422; 514/654; 514/655; 548/518; 562/899
[58] Field of Search ................ 564/374, 384; 562/899; 548/518; 514/654, 655, 422

[56] References Cited

U.S. PATENT DOCUMENTS

| | | | |
|---|---|---|---|
| 4,730,053 | 3/1988 | Dereu | 564/374 |
| 4,910,313 | 3/1990 | Welter | 564/374 |

OTHER PUBLICATIONS

Epp. O., Ladenstein, R., Wendel, A. (1983), Eur. J. Biochem., 133:51–69 (Exhibit A).
Reich, N. J., Jasperse, C. P. (1987) J. Am. Chem. Soc., 109:5549–5551 (Exhibit B).
Klein, K. P., Hauser, C. R. J. (1967) Org. Chem., 32:1479–1483 (Exhibit C).
Gould, E. S., McCullough, J. D., (1951) J. Am. Chem Soc., 73:1109–1112 (Exhibit D).

Primary Examiner—Robert Gerstl
Attorney, Agent, or Firm—John P. White

[57] ABSTRACT

The present invention provides compounds having glutathione peroxidase activity and, therefore, are effective glutathione peroxidase replacements. These compounds are useful as drugs for the prevention of cataracts and as anti-oxidants for $H_2O_2$ and other peroxides. The present invention also provides methods and pharmaceutical compositions of the compound.

28 Claims, 3 Drawing Sheets

COMPOUNDS HAVING GLUTATHIONE PEROXIDASE ACTIVITY AND USE THEREOF

This invention was made With support under Grant Numbers NEI EY00423 and GM-29259 from the National Institutes of Health, U.S. Department of Health and Human Resources. Accordingly, the U.S. Government has certain rights in the invention.

BACKGROUND OF THE INVENTION

Throughout this application, various publications are referenced by Arabic numerals within parentheses. Full citations for these publications may be found at the end of the specification immediately preceding the claims. The disclosures of these publications in their entirety are hereby incorporated by reference into this application in order to more fully describe the state of the art as known to those skilled therein as of the date of the invention described and claimed herein.

Glutathione peroxidase is a selenoenzyme composed of four identical subunits of 21,000 Da which catalyzes the reduction of $H_2O_2$ and other hydroperoxides (1, 2). In many tissues, such as the lens of the eye, glutathione peroxidase is the major defense against hydroperoxides (3). Researchers have implicated hydrogen peroxide damage as a major cause in the formation of cataracts. Glutathione 1 has the formula $H_2N\gamma Glu$-Cys-Gly-OH and is utilized as a cofactor, supplying the electrons for the reductive reaction:

$$ROOH + 2GSH \rightarrow ROH + H_2O + GSSG \qquad (eq\ 1).$$

Figure 1:
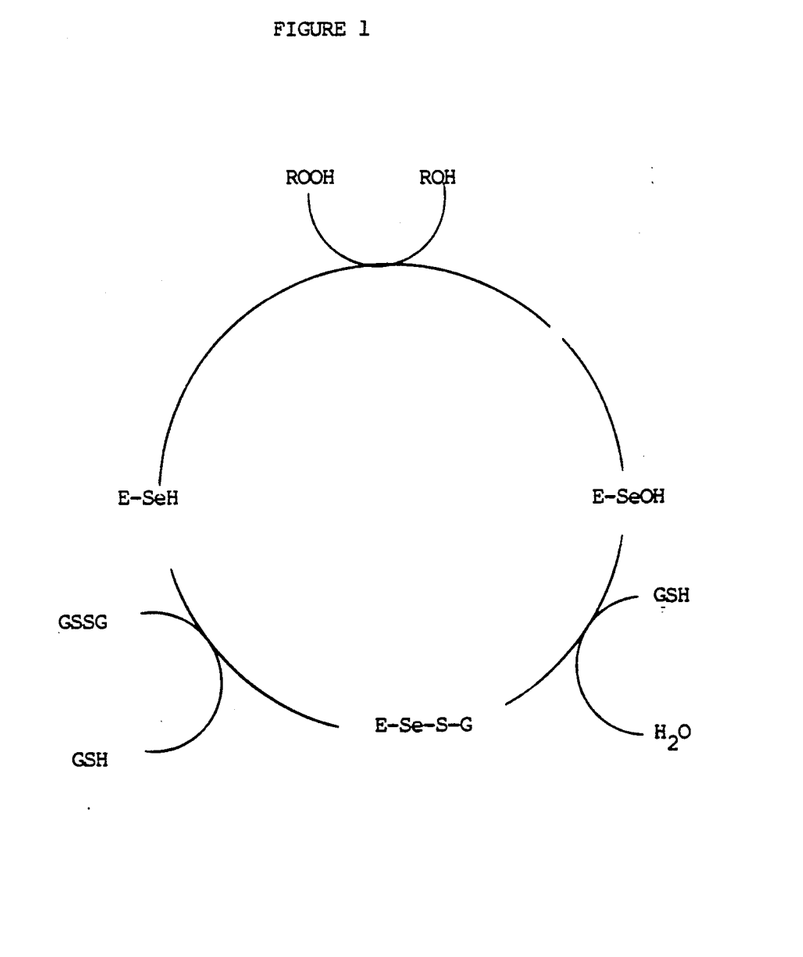
FIG. 1 illustrates the two-step reduction of seleninic acid utilizing 2 mol of GSH/mol of enzyme.

The X-ray crystal structure of GSH peroxidase has been determined with 0.2-nm resolution. The results from such analyses, as well as biochemical data have been used to develop a reaction mechanism for the reaction (2). The mechanism in FIG. 1 shows the selenium atom going from a selenol (E-Se-H) to a selenenic acid (ESeOH). In the presence of high concentrations of peroxide, it can be further oxidized to a seleninic acid (E-SeOOH). Thus, FIG. 1 illustrates the twostep reduction of selenic acid utilizes 2 mol of GSH/mol of enzyme.

Earlier work, in this laboratory, directed toward the development of compounds having GSH peroxidase activity, met with only limited success (4). This work was based on the design of small molecules which would mimic the structure of the active site of the enzyme containing the essential selenocystine residue. The most active compound produced in this study, 2, proved to be only 0.033 as active as the Ebselen compound, 3, the most active compound previously known (5).

2

Figure 2:
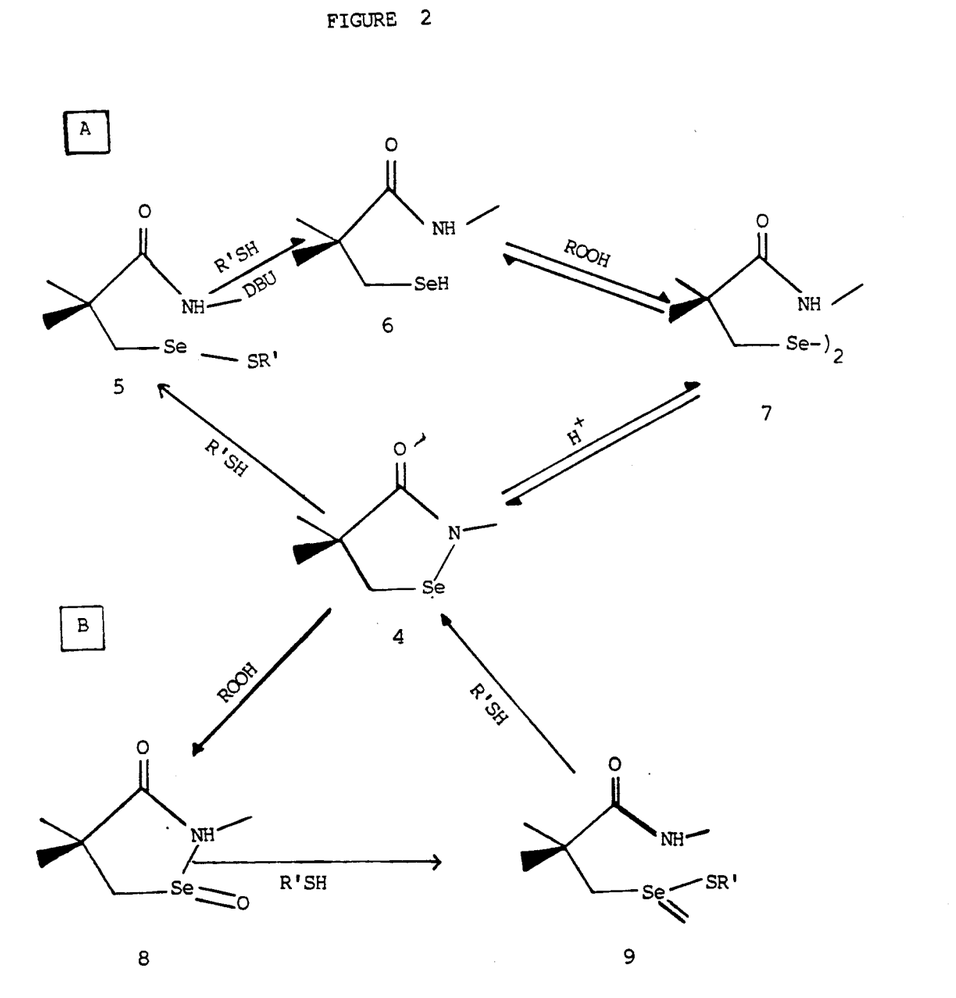
FIG. 2 is a diagram of the oxidation-reduction chemistry of 4.

Recently, a report by Reich and Jasperse (6) described the oxidation-reduction chemistry of 4 (FIG. 2). The results of this study suggest that two mechanistic pathways, A and B, are possible for the catalysis of 4 of the reduction of hydroperoxides by thiols. The following observations were especially interesting from a mechanistic viewpoint:

(1) under acid catalysis, the selenamide, 4, equilibrates with seleninamide, 8, and diselenide, 7. These compounds are produced by disproportionation of the selenenamide, 4;

(2) oxidation of 6 with MCPBA first gave the diselenide, 7, and then the seleninamide 8;

(3) oxidation of 4 produced the seleninamide, 8, and the oxidation rate was faster than the oxidation rate of the diselenide;

(4) under weakly acidic conditions, treatment of 4 with thiols gave the selenosulfide 5 and disulfide; and (5) neither the selenosulfide 5 nor diselenide 7 reacted with thiol under neutral conditions. However, upon addition of a strong amine base (DBU), both gave the selenolate and disulfide.

These results suggest some guidelines for the construction of molecules showing GSH activity:

(1) more easily available diselenides would function as effectively as the more difficult to construct cyclic compounds in the production of the catalytically active species (observations 1–4 above); and (2) inclusion in the molecule of a strongly basic group proximal to the active selenium atom is desirable as it would be expected to catalyze the reaction of thiols with the intermediate diselenide and selenosulfide. Presumably, the base functions to provide a source of nucleophilic thiolate anion (observation 5 above).

Figure 3:
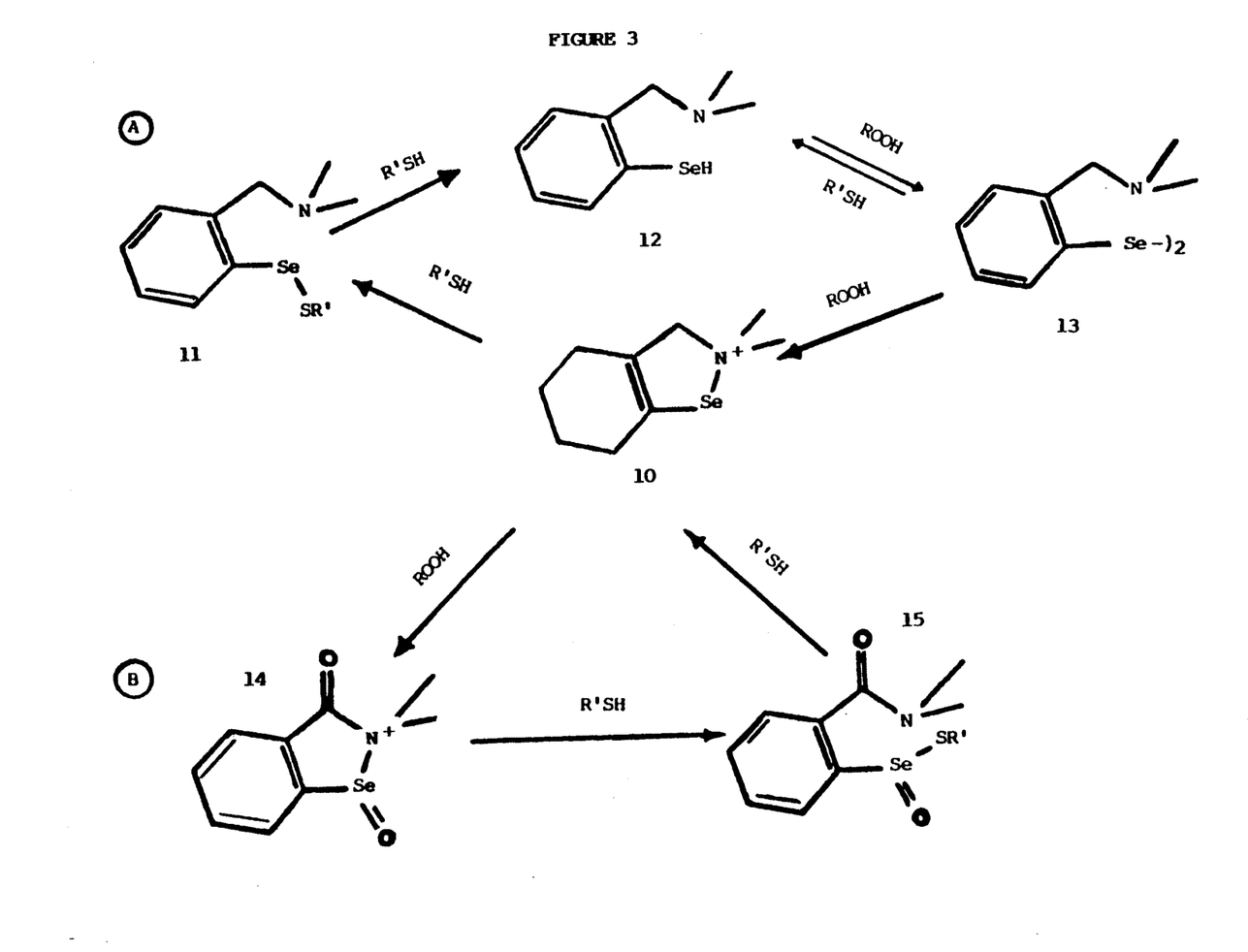
FIG. 3 illustrates chemical process for producing tertiary amines with glutathione peroxidase activity.

With these guidelines in mind, we chose as compounds for study, tertiary amines of the type 3 (FIG. 3). The use of tertiary amines seemed preferable to that of primary or secondary amines since intermediate 10 and 14 are not stable compounds and are thus activated toward nucleophilic attack by thiol at the selenium atom.

SUMMARY OF THE INVENTION

The present invention provides a compound having the structure:

wherein n is an integer between 1 and about 30; wherein each $R_1$ may be the same or different and represents an electron donor group or hydrogen; wherein each $R_2$ may be the same or different and represents a lower alkyl group or hydrogen; wherein $R_3$ represents a hydrogen atom which may be present or absent, which if present results in a positive charge on N; wherein each $R_4$ may be the same or different and represents a lower alkyl group or hydrogen; wherein Z represents a selenium, a tellurium, or a sulfur atom; and wherein the dashed lines represent carbon-carbon bonds which may be present or absent.

Additionally, the invention provides another compound which has the structure:

wherein n is an integer between 1 and about 30; wherein each $R_1$ may be the same or different and represents an electron donor group or hydrogen; wherein each $R_2$ may be the same or different and represents a lower alkyl group or hydrogen; wherein each $R_3$ may be the same or different and represents a lower alkyl group or hydrogen; wherein $R_4$ may be the same or different and represents a lower alkyl group or hydrogen; wherein $R_5$ may be the same or different and represents a lower alkyl group or hydrogen; wherein $R_6$ represents a hydrogen atom which may be present or absent, which if present results in a positive charge on N; and wherein Z represents a selenium, a tellurium, or a sulfur atom.

The present invention also provides a method of reducing $H_2O_2$ which comprises contacting $H_2O_2$ with an amount of the above-described compounds of this invention effective to reduce $H_2O_2$.

Further, the invention provides a method of treating a $H_2O_2$-induced condition in a subject which comprises administering to the subject an amount of either of the above-described compounds of this invention effective to reduce $H_2O_2$-induced condition.

Finally, the invention provides a pharmaceutical composition which comprises an amount of either of the above-described compounds of this invention effective to reduce $H_2O_2$ in a subject afflicted with a $H_2O_2$-induced condition and a pharmaceutically acceptable carrier.

DETAILED DESCRIPTION OF THE INVENTION

The present invention provides a compound having the structure:

wherein n is an integer between 1 and about 30 wherein each $R_1$ may be the same or different and represents an electron donor group or hydrogen; wherein each $R_2$ may be the same or different and represents a lower alkyl group or hydrogen; wherein $R_3$ represents a hydrogen atom which may be present or absent, which if present results in a positive charge on N; wherein each $R_4$ may be the same or different and represents a lower alkyl group or hydrogen; wherein Z represents a selenium, a tellurium, or a sulfur atom; and wherein the dashed lines represent carbon-carbon bonds which may be present or absent.

As used herein, an electron donor is a group of atoms, in an organic molecule, which gives electrons to the remaining atoms in the molecule. Examples of electron donors include, but are not limited to, $-CH_3$, $-OH$, and $CH-O$. This group produces an inductive or a mesomeric effect.

Further, the invention provides the above-described compound wherein Z represents the selenium atom. Further still, n is preferably from about 1 to about 5.

The compounds described herein are synthetic mimics of glutathione peroxidase and therefore are effective glutathione peroxidase replacements. These compounds are useful as drugs for the prevention of cataracts, especially maturity onset cataract development. Further, these compounds are useful as anti-oxidants for $H_2O_2$ and other peroxides.

Moreover, when using these compounds as drugs, glutathione or derivatives thereof may be added to the compounds of the invention, functioning as drug carriers which facilitate administration of the compounds.

In the structure, $R_1$ may be a thiol or an alkyl group containing a thiol. Further, both $R_1$ may be simultaneous thiols. Moreover, $R_1$ may be $-SH$ or $-S-CH_3$.

Additionally, the invention provides a compound having the structure:

including a salt, e.g. a chloride salt, of the compound.

The invention also concerns a compound having the structure:

including a salt, e.g., a chloride salt, of the compound.

The invention further provides a compound having a structure:

The invention also provides a compound having a structure:

This invention still further provides a compound having a structure:

The invention also provides a compound having a structure:

Further, the invention provides a compound having a structure:

The present invention provides a compound having a structure:

The present invention additionally provides compound having a structure:

The present invention additionally provides compound having a structure:

The present invention also concerns a method of reducing $H_2O_2$ which comprises contacting $H_2O_2$ with an amount of the compound of having the structure:

effective to reduce $H_2O_2$.

Further, the invention provides a method of treating a $H_2O_2$-induced condition in a subject, e.g. a human subject, which comprises administering, e.g. by topical, intravenous, intraperitoneal, intramuscular, intradermal, or subcutaneous administration, to the subject an amount of the compound having the structure:

effective to reduce $H_2O_2$ in the subject and thereby treat the $H_2O_2$-induced condition. It is worthy to point out at this time that the administration of the compound to the subject may be effected by means other than those listed herein. Further, the H₂O₂-induced condition may involve cataracts or inflammation of a tissue. Where the H₂O₂-induced condition involves cataracts, administration is effected by, but is not limited to, topical contact to the surface of an eye.

The present invention also concerns a method of reducing H₂O₂ which comprises contacting H₂O₂ with a suitable amount of any of the compounds of the invention effective to reduce H₂O₂.

Additionally, the invention provides a method of treating a H₂O₂-induced condition in a subject which comprises administering to the subject an amount of any of the compounds of the invention effective to reduce H₂O₂ in a subject and thereby treat the H₂O₂-induced condition.

The present invention also concerns a compound having the structure:

wherein n is an integer between 1 and about 30; wherein each $R_1$ may be the same or different and represents an electron donor group or hydrogen; wherein each $R_2$ may be the same or different and represents a lower alkyl group or hydrogen; wherein each $R_3$ may be the same or different and represents a lower alkyl group or hydrogen; wherein $R_4$ may be the same or different and represents a lower alkyl group or hydrogen; wherein $R_5$ may be the same or different and represents a lower alkyl group or hydrogen; wherein $R_6$ represents a hydrogen atom which may be present or absent, which if present results in a positive charge on N; and wherein Z represents a selenium, a tellurium, or a sulfur atom.

In the above-described compound, n is preferably from about 1 to about 5. Further, Z is a selenium atom.

The invention additionally provides a method of reducing H₂O₂ which comprises contacting H₂O₂ with an amount of the compound having the structure:

effective to reduce H₂O₂.

Further, the invention provides a method of treating a H₂O₂-induced condition in a subject, e.g. a human subject, which comprises administering, e.g. by topical, intravenous, intraperitoneal, intravascular, intradermal, of subcutaneous administration, to the subject an amount of the compound having the structure:

effective to reduce H₂O₂ in the subject and thereby treat the H₂O₂-induced condition.

In this method the H₂O₂-induced condition may involve cataracts, in such cases, administration may be effected, but is not necessarily limited to, topical contact on to the surface of the eye. Further in this method, the H₂O₂-induced condition may involve inflammation of a tissue.

Additionally, the invention provides a method of reducing H₂O₂ which comprises contacting H₂O₂ with an amount of the compounds previously described which are derived from the compound having the structure:

effective to reduce H₂O₂

Further, the present invention also provides a method of treating a H₂O₂-induced condition in a subject which comprises administering to the subject an amount of the compounds previously described which are derived from the compound having the structure:

effective to reduce it H₂O₂ in a subject and thereby treat the H₂O₂-induce condition.

The present invention additionally provides a method of reducing which comprises contacting H₂O₂ with an amount of a compound having the structure:

effective to reduce H₂O₂.

The invention further provides a method of reducing $H_2O_2$ which comprises contacting $H_2O_2$ with an amount of a compound having the structure:

effective to reduce $H_2O_2$.

Moreover, the invention concerns a method of reducing $H_2O_2$ which comprises contacting $H_2O_2$ with an amount of a compound having the structure:

effective to reduce $H_2O_2$.

The present invention also concerns a method of reducing $H_2O_2$ which comprises contacting $H_2O_2$ with an amount of a compound having the structure:

effective to reduce $H_2O_2$.

The present invention provides a method of reducing $H_2O_2$ which comprises contacting $H_2O_2$ with an amount of a compound having the structure:

effective to reduce $H_2O_2$.

Another provision concerns a method of reducing $H_2O_2$ which comprises contacting $H_2O_2$ with an amount of a compound having the structure:

effective to reduce $H_2O_2$.

Further, the invention provides method of reducing $H_2O_2$ which comprises contacting $H_2O_2$ with an amount of a compound having the structure:

effective to reduce $H_2O_2$.

Further still the invention provides a method of reducing $H_2O_2$ which comprises contacting $H_2O_2$ with an amount of a compound having the structure:

effective to reduce $H_2O_2$.

Additionally, the invention concerns a method of reducing $H_2O_2$ which comprises contacting $H_2O_2$ with an amount of a compound having the structure:

effective to reduce $H_2O_2$.

The invention also provides a pharmaceutical composition which comprises an amount of either of the compound having the structure:

or having the structure:

effective to reduce $H_2O_2$ in a subject afflicted with a $H_2O_2$-induced condition and a pharmaceutically acceptable carrier.

Further, the invention provides a pharmaceutical composition which comprises an amount of any of the compounds of the invention effective to reduce $H_2O_2$ in a subject application with a $H_2O_2$-induced condition and a pharmaceutically acceptable carrier.

As used herein, the term "pharmaceutically acceptable carrier" encompasses any of the standard pharmaceutical carriers such as sterile solutions, tablets, coated tablets and capsules. Typically such carriers contain excipients such as starch, milk, sugar, certain types of clay, gelatin, stearic acids or salts thereof, magnesium or calcium sterate, talc, vegetable fats or oils, gums, glycols, or other known excipients. Such carriers may also include flavor and color additives or other ingredients. Compositions comprising such carriers are formulated by well known conventional methods.

This invention is illustrated in the Experimental Details section which follows. This section is set forth to aid in an understanding of the invention but is not intended to, and should not be construed to, limit in any way the invention as set forth in the claims which follow.

EXPERIMENTAL DETAILS

Materials and Methods

All reactions were carried out under a nitrogen atmosphere. Melting points were determined in a Thomas capillary melting point apparatus and are uncorrected. PMR spectra were recorded on a General Electric QE-300 Spectrometer using the specified solvent. GC-MS analyses were obtained on a Hewlett-Packard 5992B GC/MS system equipped with a capillary column. Exact masses were obtained from the NIH Rockefeller Mass Spectrometry Biotechnology Resource at Rockefeller University, New York, N.Y., by positive chemical ionization(CI). Gas chromatographic (GC) analyses were performed on a Varian Model 3700 gas chromatograph (flame ionization detector) using 1/8-in. columns packed with 2% OV-101-0.2% Carbowax on Chromasorb G. The standard temperature program is 60° C. (1 min) up to 300° C. at 20° C./min.

[2-[(N,-N-Dimethylamino)methyl]phenyl]lithium 17. n-Butyllithium (0.2 mol, 80 mL of a 2.5M solution in hexanes) was placed in a round-bottomed flask under nitrogen. N,N-dimethylbenzylamine (13.5g, 0.1 mol) and 215 mL of dry ether were added, and the resulting solution was allowed to stir at room temperature for 20 h. This was used as the stock solution of 17 and was approximately 0.34M in 17.

2,2,-Diselenobis[[(N,N-dimethylamino)methyl]benzene]Bis(ydrochloride salt) 19. Under a nitrogen atmosphere, 2.0 g (25.3 mmol) of metallic selenium was added to 40 mL (13.6 mmol) of the stock solution of 17, and the mixture stirred at room temperature for 1 h.

The resulting mixture (slightly green) was quenched by the addition of water and ether followed by bubbling air through it for 1 h. Layers were separated, and the aqueous phase was extracted with several portions of ether. The combined ethereal phases were washed with water and extracted with a 6M HCl, solution. The combined extracts were concentrated in vacuo to give an oily residue, 18. This oil solidified upon trituration with ethanol-benzene to give bis(hydrochloride salt), 19, as an orange powder. Precipitation from ethanolbenzene provided 621 mg (21.4%) of yellow powder (darkenting at 219° C. mp 224°-225° C. dec): GC retention time (free base)=8.56 min: TLC (free base, silica gel, 20% ethyl acetate-ligroin) $R_f=0.35$; $^1$H NMR (300 MHz, $D_2O$) $\delta 7.73$ (d, 1 H, 4.2 Hz), 7.45 (m,2 H), 7.36 (m, 1 H), 3.98 (s, 2 H), 2.67 (s, 6 H); HRMS (from free base/Cl) $(C_{18}H_{25}N_2$ $Se_2)H^+$ 429.0222 [calculated for $(C_{18}H_{25}N_2Se_2)H^+$ 429.0348].

1-Bromo-2-(pyrrolidin-1-ylmethyl benzene 22. 2-Bromobenzyl bromide 21 (3.0 g, 12 mmol) was dissolved in 5 mL of methylene chloride, and 2 equiv (22.4 mmol, 2.2 mL) of pyrrolidine 2o was added dropwise. The initial reaction was exothermic. After the addition was complete, the mixture was allowed to stir at room temperature overnight; it was then poured into water and ether, the layers were separated, and the ether layer was washed with water, dried (KOH), and concentrated to a yellow oil. Distillation provided 2.346 g (81%) of the amine 22, boiling at 104°-107° C.(20 mmHg): GC retention time 3.92 min; TLC (silica gel, 20% ethyl acetate-ligroin) $R_f=0.39$; IR (neat) 2950, 2780, 1600, 1450, 1430, 1025, 750; 1 H NMR (300MHz,$CDCl_3$) $\delta 7.54$ (m, 2 H), 7.28 (m, 1 H), 7.09(m, 1 H), 3.74 (s, 2 H), 2.60 (m, 4 H), 1.81 (m, 4 H); GC-MS(% abundance) 241 (70), 240 (100), 239 (71), 238 (93), 171(43), 169 (45), 84 (57), 70 (20), 42 (43).

2,2,-Diselenobis(pyrrolidin-1-ylmethyl)benzene] Bis (hydrochloride salt) 25. The bromide 22 (480 mg, 2 mmol) was dissolved in 4 mL of dry THF and the resulting solution cooled to −78° C. n-Butyllithium (2.0 mL of a 2M solution in hexanes, 2 equiv) was added dropwise via syringe. After the addition was complete, the mixture was stirred at −78° C. for 1 h. Selenium (2 equiv, 4 mmol, 316 mg) was added followed by anhydrous $MgBr_2$ (4mmol). This mixture was allowed to stir overnight. Selenium (2 portions of 35 mg each) was added, and the mixture turned dark red. The mixture was then poured into water and ether, the ether layer was separated, and the aqueous phase was extracted with ether. The combined ethereal extracts were dried ($Na_2SO_4$) and concentrated to give an oily residue. The residue was taken up in 6M HCl solution and the solution washed with methylene chloride several times. The aqueous solution was then concentrated in vacuo to give a resinous residue (432 mg). This material was dissolved in the minimum amount of ethanol, benzene was added, and the compound was allowed to precipitate. This procedure provided 250 mg (45%) of 25 as a yellow powder (darkening at 216° C., mp 229°-230° C. dec): GC retention time (free base)=10.12 min; TLC (free base, silica gel, 20% ethyl acetate-ligroin) $R_f=0.21$; $^1$H NMR (300MHz, $D_2O$) $\delta 7.73$ (d, 1 H, 4.2 Hz), 7.45 (m, 2 H), 7.36 (m, 1 H), 4.09 (s, 2 H), 3.30 (m, 2 H), 2.95 (m, 2 H), 1.99 (m, 2 H), 1.83 (m, 2 H); HRMS (from free base/Cl) $(C_{22}H_{28}Se_2)H^+ 481.0661$ [calculated for $(C_{22}H_{28}N_2 Se_2)H^+$ 481.0654].

[2-[(N3N-Dimethylamino)methyl]phenyl]seleno]benzene 26. The aryl)ithium, 17 (20 mL 6.6 mmol) solution was placed in a flask under nitrogen. Diphenyl diselenide (2.375 g, 7.6 mmol) in 20 mL of dry ether was added dropwise over the course of 5 min. The resulting solution was allowed to stir at room temperature for 1 h. The solution was diluted with ether, washed well with water, dried ($Na_2SO_4$), and concentrated. The yellow residual oil was distilled (kugelrohr, 0.5 Torr) at 145°-155° C. (yield 1.302 g, 68%). Material obtained in this way contained a small amount of diphenyl diselenide. This impurity could be removed by purification by preparative TLC on silica gel eluting with 20% ethyl acetate-ligroin containing 1% triethylamine ($R_f=0.38$). In this way 145 mg of distilled material gave 101 mg of purified 26 as a tan, mobile oil. Upon standing at room temperature, the oil solidified to a waxy, tan solid (mp48° C.): GC retention time=5.88 min; $^1$H NMR (300MHz, CDCl$_3$) δ7.56-7.0 (m, 9 H), 3.52(s, 2 H), 2.24 (s, 6 H); GC-MS (% abundance) 291 (82), 276, (30), 165 (52), 132 (59), 121 (100), 91 (32), 58 (57).

[[2-(Pyrrolidin—1-ylmethy)phenyl]soleno]benzene 27. The bromide 22 (240 mg, 1 mmol) was dissolved in 3 mL of dry THF and the resulting solution cooled to −78° C. under nitrogen. n-Butyllithium (2 equiv, 2 mmol, 1 ml of a 2.0M solution in hexanes) was added dropwise via syringe and the mixture stirred for an additional hour at −78° C. after the addition was complete. Diphenyl diselenide (1 equiv, 1 mmol, 212 mg) in 5 mL of THF was added dropwise and the mixture stirred overnight. A few drops of saturated ammonium chloride solution were added, salts were filtered, and the solution was concentrated to give the crude 27. Purification by preparative TLC on silica gel, eluting with 20% ethyl acetate-ligroin containing 1% triethylamine R$_f$=0.42), gave pure 27 ( 104 mg, 33%): GC retention time=7.12 min; $^1$H NMR (300MHz, CDCl$_3$) δ7.56-7.0 (m, 9 H), 3.75 (s, 2 H), 2 52 (m, 4 H), 1.77 (m, 4 H).

Synthesis of Amines

Diphenyl diselenide, 16 was obtained from Aldrich and used without further purification.

16

Diaminodiselenide 18 Was synthesized in two steps from commercially available materials eq 1). Orthometalation of N,N-dimethylbenzylamine was readily accomplished according to procedure of Klein and Hauser (7). Thus, N,N-dimethylbenzylamine was treated with a slight excess of n-butyllithium in ether-hexane at room temperature for 24 h and the resulting solution of aryllithium 17 treated with metallic selenium. The resulting arylselenol was oxidized with air to the corresponding diselenide (8). The oily product was most easily handled as its bis(hydrochloride salt) 19.

The amine 22 required for the synthesis of 24 was readily prepared by alkylation of pyrrolidone 20 with 2-bromobenzyl bromide 21. The corresponding Grignard reagent failed to form upon treatment of 22 with magnesium. Halogen-metal exchange with 2 equiv of nbutyllithium at −78° C. in THF proceeded smoothly to give the desired aryllithium 23. This reagent readily reacted with metallic selenium in the presence of anhydrous MgCl$_2$ to give the desired diselenide 24. As in the case of 18, the diselenide was converted for ease of handling into the bis(hydrochloride salt) 25.

The synthesis of the diaryl selenide, 26 was accomplished in a straightforward manner by the reaction of aryllithium, 17 with diphenyl diselenide. Diaryl selenide 26 proved to be much easier to handle than the corresponding diselenides and could thus be purified by chromatography.

26

The synthesis of the diaryl selenide, 27 was achieved by the reaction of aryllithium, 23, with diphenyl diselenide.

27

Results and Discussion

Glutathione peroxidase activity of the compounds was determined with a modification of the method of Wendel (9) using hydrogen peroxide as the substrate in the presence of GSH. Glutathione reductase was used to reduce the oxidized GSH with NADPH as a cofactor (eq 2). The decrease in NADPH monitored spectrophotometrically at 366 nm is a measure of GSH peroxidase activity (see eq 2-4). The assay mixture (700 μL) contains 50 mM potassium phosphate buffer, pH 7.0, 1 mM EDTA, 1 mM sodium azide, 1 mM GSH, 0.25 mM NADPH, 1 unit of GSSG reductase, and an appropriate amount of test compound (usually 2-20 μM final concentration). The absorbance at 366 nm was recorded for a few minutes to estimate the background and stability of the preparation. Reaction was initiated by the subsequent addition of hydrogen peroxide to 500 μM. Appropriate blanks were run in the absence of test compound and in some cases with test compound and $H_2O_2$ in the absence of NADPH. The results are shown in Table I. The relative activities of the compounds prepared in this study were compared to that of GSH peroxidase. Values for Ebselen 3 and compound 2 and are included.

For most compounds, the initial rate of NADPH utilization was determined at six concentrations ranging over more than a 10-fold difference in concentration. The rates in all cases were found to be a linear function of concentration, suggesting that the compounds were saturated with substrate. Under such conditions, the initial rates can be assumed to be maximum rates and $V_{max}=kE_t$, where V = maximum velocity of the reaction and $E_T$ represents the total concentration of the GSH peroxidase analogue. The K value represents the turnover number, i.e., the number of $H_2O_2$ molecules degraded per minute per molecule of analog. These values are shown in Table I. It was found that the reaction rates remain linear for at least 5 min. Thus, for example, for 25, 55.5 molecules of $H_2O_2$ are degraded per molecule of compound in five minutes without any loss of catalytic activity. No indication of loss of catalytic activity was observed. While these turnover numbers are very low compared to that of GSH peroxidase, they are in the same range as have been reported for enzymes such as lysozyme (30 μ mole per minute per μ mole).

Several conclusions can be drawn from these results. The observation that diphenyl diselenide 16 exhibits approximately twice the activity of Ebselen's 3 rules out the assumption that a selenium-nitrogen bond is necessary for glutathione peroxidase activity. This conclusion was tentatively suggested by the activity found in 2. It is also consistent with the ovservations of Reich and Jasperse (6) since one could reasonably propose that the catalytic cycle A (FIG. 2.) completely by passes the selenamide, 4 with nucleophilic attack of thiolate occurring on the diselenide 7. Support of this view is found in the observation that oxidation of 6 led to the formation of 7 and not 4(6)

TABLE I

| Compound | Activity[a] | rel GSH Peroxidase Activity[b] |
|---|---|---|
| 2 | 0.034 | 0.03 |
| 3 | 0.99 | 0.88 |
| 16 | 1.95 | 1.7 |
| 26 | 0.050 | 0.043 |
| 27 | 0.046 | 0.04 |
| 19 | 10.5 | 9.1 |
| 25 | 11.1 | 9.7 |

[a] Micromoles of NADPH utilized per minute per micromole.
[b] Based upon GSH peroxidase activity equal to 10,000.

Also clear from the results in the table is the requirement that the disubstituted selenium atom must have at least one selenium-heteroatom bond. The diaryl selenides 26 and 27 show small amounts of activity. This activity may be due to trace amounts of dimethyl diselenide present in the compounds as impurities remaining from their syntheses.

The tertiary amine analogue of 16, 19, and 25 are approximately 5.5-fold more active than 16. The role of the tertiary amine in the catalysis of the reaction may be that which was suggested earlier. The amine may serve to deprotonate the thiol sulfhydryl group and thus provide a high local concentration of nucleophilic thiolate anion. Another possible mode of catalysis might be that the conjugate acid of the amine, the ammonium ion, obtained upon abstraction of a proton from a sulfhydryl group serves as a proton source, facilitating the reduction of hydrogen peroxide to water.

The most active compounds, 19 and 25, are approximately 10 . 5 times more active than Ebelson 3 and indicate that it is possible to produce relatively simple compounds that have significant GSH peroxidase activity.

In summary, we prepared organoselenium compounds which show catalytic activity in the enzyme assay for the selenoenzyme glutathione peroxidase. These compounds were designed on the basis of the known chemistry of models for the active site of glutathione peroxidase. Diphenyl diselenide 16 has been shown to be approximately 2-fold more active in this assay then the most active compound previously known. Introduction of tertiary amine substituents onto the aromatic nucleus at a position ortho to the selenium atom in 19 and 25 results in a further approximately 5-fold increase in activity. Diaryl selenides 26 and 27 are demonstrated to show no significant glutathione peroxidase activity.

REFERENCES

1. Chance, B. Boveris, A., Nakase, Y., Sies, H. (1978 Functions of Glutathione in Liver and Kidney (Springer Verlag, Berlin,), pp 95–106.
2. Epp, O, Ladenstein, R., Wendel, A. (1983) Eur. J. Biochem. 133:51–69.
3. Spector, A. (1984) Invest. Ophthal. Vis. Sci. 1984, 25:130–146.
4. Unpublished Observations.
5. Wendel, A. (1985) European Patent, 165:534.
6. Reich, N. J., Jasperse, C. P. (1987) J. Am. Chem. Soc., 109:5549-5551.
7. Klein, K. P., Hauser, C. R. J. (1967) Org. Chem., 32:1479–1483.
8. Gould, E. S., McCullough, J. D. (1951) J. Am. Chem Soc., 73:1109–1112. 1
9. Wendel, A. (1981) Methods Enzymol, 77:325–333.

What is claimed is:
1. A compound having the structure:

wherein n is an integer between 1 and 30;
wherein each $R_1$ may be the same or different and is a thiol, thiolmethyl lower alkyl group or hydrogen;
wherein each $R_2$ may be the same or different and is a lower alkyl group or hydrogen;
wherein $R_3$ is a hydrogen atom which may be present or absent, which if present results in a positive charge on N;
wherein each $R_4$ may be the same or different and is a lower alkyl group or hydrogen; p1 wherein $X^-$ is an anion which is present if $R_3$ is present and which is absent if $R_3$ is absent; and
wherein the dashed lines present carbon-carbon bonds which amy be present or absent.
2. A compound of claim 1, wherein n is from 1 to 5.
3. A compound of claim 1, wherein one or more $R_1$ are hydrogen.
4. A compound of claim 1, wherein one or more $R_1$ are lower alkyl groups.
5. A compound of claim 1, wherein one or more $R_1$ are thils.
6. A compound of claim 5, wherein one or more $R_1$ are —SH.
7. A compound of claim 5, wherein both $R_1$ are thiols.
8. A compound of claim 1, wherein one or more $R_1$ are thiomethyls.
9. A compound of claim 8, wherein one or more $R_1$ are —$SCH_3$.
10. A compound of claim 1, wherein one or more $R_1$ are —SH or —$SCH_3$.
11. A compound of claim 1 having the structure:

12. A compound of claim 11, wherein $X^-$ is a chloride ion.
13. A compound of claim 1 having the structure 14. A compound of claim 13, wherein $X^-$ is a chloride ion.
15. A compound of claim 1 having the structure:

16. A compound having the structure:

wherein n is an integer between 1 and 30;
wherein each $R_1$ may be the same or different and is a thiol, thiomethyl, lower alkyl group or hydrogen;
wherein each $R_2$ may be the same or different and is a lower alkyl group or hydrogen;
wherein each $R_3$ may be the same or different and is a lower alkyl group or hydrogen;
wherein $R_4$ is a lower alkyl group or hydrogen;
wherein $R_5$ is a lower alkyl group or hydrogen;
wherein $R_6$ is a hydrogen atom which may be present or absent, which if present results in a positive charge on N; and
wherein $X^-$ is an anion which is present if $R_6$ is present and which is absent if $R_6$ is absent.
17. A compound of claim 16, wherein n is from 1 to 5.
18. A compound of claim 16, wherein one or more $R_1$ are hydrogen.
19. A compound of claim 16, wherein one or more $R_1$ are lower alkyl groups.
20. A compound of claim 16, wherein one or more $R_1$ are thiols.

21. A compound of claim 20, wherein one or more $R_1$ are —SH.

22. A compound of claim 20, wherein both $R_1$ are thiols.

23. A compound of claim 16, wherein one or more $R_1$ are thiomethyls.

24. A compound of claim 23, wherein one or more $R_1$ are —SCH$_3$.

25. A pharmaceutical composition which comprises an amount of a compound of claim 1 or 16 effective to reduce $H_2O_2$ in a subject afflicted with $H_2O_2$-induced condition and a pharmaceutically acceptable carrier.

26. A pharmaceutical composition which comprises an amount of a compound of any of claims 2-15 or 17-24 effective to reduce $H_2O_2$ in a subject afflicted with a $H_2O_2$-induced condition and a pharmaceutically acceptable carrier.

27. A pharmaceutical composition of claim 25, wherein the pharmaceutical composition further comprises a cofactor.

28. A pharmaceutical composition of claim 27, wherein the cofactor is gluthathione.

* * * * *